United States Patent
Simeth et al.

(10) Patent No.: US 9,724,179 B2
(45) Date of Patent: Aug. 8, 2017

(54) HEAD PORTION AND HANDLE PORTION OF AN ORAL CARE DEVICE

(71) Applicant: Braun GmbH, Kronberg (DE)

(72) Inventors: Martin Simeth, Konigstein (DE); Philipp Jung, Griesheim (DE); Thomas Fritsch, Eppstein (DE)

(73) Assignee: BRAUN GMBH, Kronberg (DE)

( * ) Notice: Subject to any disclaimer, the term of this patent is extended or adjusted under 35 U.S.C. 154(b) by 300 days.

(21) Appl. No.: 14/532,775

(22) Filed: Nov. 4, 2014

(65) Prior Publication Data
US 2015/0052696 A1    Feb. 26, 2015

Related U.S. Application Data

(63) Continuation of application No. 13/741,403, filed on Jan. 15, 2013, now abandoned.

(30) Foreign Application Priority Data

Jan. 17, 2012  (EP) ..................... 12151340

(51) Int. Cl.
*A61C 17/22*    (2006.01)
*A61C 17/34*    (2006.01)
(Continued)

(52) U.S. Cl.
CPC ........ *A61C 17/221* (2013.01); *A46B 15/0004* (2013.01); *A46B 15/0008* (2013.01);
(Continued)

(58) Field of Classification Search
CPC . A46B 15/00; A46B 15/0002; A46B 15/0004; A46B 15/0008; A46B 13/00; A46B 13/02; A61C 15/047; A61C 17/00; A61C 17/02; A61C 17/0202; A61C 17/16; A61C 17/22; A61C 17/221; A61C 17/222; A61C 17/225; A61C 17/24; A61C 17/26; A61C 17/32; A61C 17/34; A61C 17/3409;
(Continued)

(56) References Cited

U.S. PATENT DOCUMENTS

2009/0087813 A1*  4/2009  Cai ................. A46B 13/02
                                                          433/89

FOREIGN PATENT DOCUMENTS

EP    1980375 A1    10/2008
GB    2030855       4/1980
(Continued)

OTHER PUBLICATIONS

European Search Report for EP 12 15 1340 dated Sep. 4, 2012.

*Primary Examiner* — Mark Spisich

(57) ABSTRACT

An oral care device is disclosed. The oral care device includes a housing being at least partly formed of an electrically isolating material; a capacitor having a first electrode and a second electrode, the first and second electrodes being electrically isolated by the electrically isolating material of the housing such that they are not exposed to an outside environment of the oral care device; and a processor unit being electrically connected to the first and second electrodes. The processor unit is arranged such that during operation of the oral care device it determines a capacitance (x) of the capacitor in order to determine whether the oral care device is within a user's oral cavity or not.

8 Claims, 3 Drawing Sheets

(51) Int. Cl.
*A46B 15/00* (2006.01)
*A61C 17/16* (2006.01)

(52) U.S. Cl.
CPC ............ *A61C 17/16* (2013.01); *A61C 17/225* (2013.01); *A61C 17/34* (2013.01)

(58) Field of Classification Search
CPC ............ A61C 17/3427; A61C 17/3436; A61B 17/244; A61H 13/00
USPC ............. 15/22.1, 28; 132/322; 433/114, 118, 433/131; 601/142, 162; 606/161
See application file for complete search history.

(56) References Cited

FOREIGN PATENT DOCUMENTS

| | | |
|---|---|---|
| JP | 3251207 | 11/1991 |
| JP | 8275961 | 10/1996 |
| WO | WO2011/077282 A1 | 6/2011 |
| WO | WO2011/077290 A1 | 6/2011 |

\* cited by examiner

HEAD PORTION AND HANDLE PORTION OF AN ORAL CARE DEVICE

CROSS REFERENCE TO RELATED APPLICATION

This application is a continuation of U.S. patent application Ser. No. 13/741,403, filed Nov. 4, 2014, now abandoned.

FIELD OF THE INVENTION

The present disclosure relates to the field of head portions and handle portions for oral care devices and generally to the field of oral care devices. More particularly, the present disclosure relates to the field of methods for determining the position of an oral care device.

BACKGROUND OF THE INVENTION

It is known that oral care devices may have an on/off switch by which a user can switch on or off the oral care device. The on/off switch can be operated independent from the location of the oral care device, in particular of the location of a head portion of the oral care device, which is intended for location in a users oral cavity.

In some instances, an appliance material may be applied to the head portion of the oral care device. In case the oral care device is switched on with the head portion being outside of a user's oral cavity, the appliance material may be splashed around by a movement of the head portion. It is thus a desire to provide an oral care device that is improved over the known oral care devices.

SUMMARY OF THE INVENTION

In one embodiment, a head portion for an oral care device is provided. The head portion includes a housing being at least partly formed of an electrically isolating material; a moveable drive member; a first electrode for forming part of a capacitor; and a first electrically conducting path for connecting the first electrode to a processor. The first electrode is electrically isolated by the electrically isolating material of the housing such that it is not exposed to an outside environment of the head portion; and wherein the drive member forms at least part of the first electrode, the drive member including a mechanical and electrical coupling for attachment to a handle portion of the oral care device.

In another embodiment, a handle portion for an oral care device is provided. The handle portion includes a processor unit being connectable to a first electrode and a second electrode of a capacitor; a motor; and a drive shaft for the transfer of rotating motion of the motor to an oscillating pivoting motion of a bristle carrier. The processor unit is arranged such that during operation of the handle portion it determines a capacitance of a capacitor formed by the first electrode and the second electrode in order to determine whether the oral care device is within a user's oral cavity or not. The drive shaft provides both mechanical coupling to a head portion and electrical coupling to the first electrode of the head portion.

In another embodiment, an oral care device is provided. The oral care device includes a housing being at least partly formed of an electrically isolating material; a capacitor having a first electrode and a second electrode, the first and second electrodes being electrically isolated by the electrically isolating material of the housing such that they are not exposed to an outside environment of the oral care device; and a processor unit being electrically connected to the first and second electrodes. The processor unit is arranged such that during operation of the oral care device it determines a capacitance (x) of the capacitor in order to determine whether the oral care device is within a user's oral cavity or not.

In another embodiment, a method for determining whether a part of an oral care device is located within a user's oral cavity is provided. The method includes the steps of determining a capacitance (x) of a capacitor formed by a first electrode and a second electrode; and comparing the determined capacitance (x) with a predetermined threshold value (z).

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
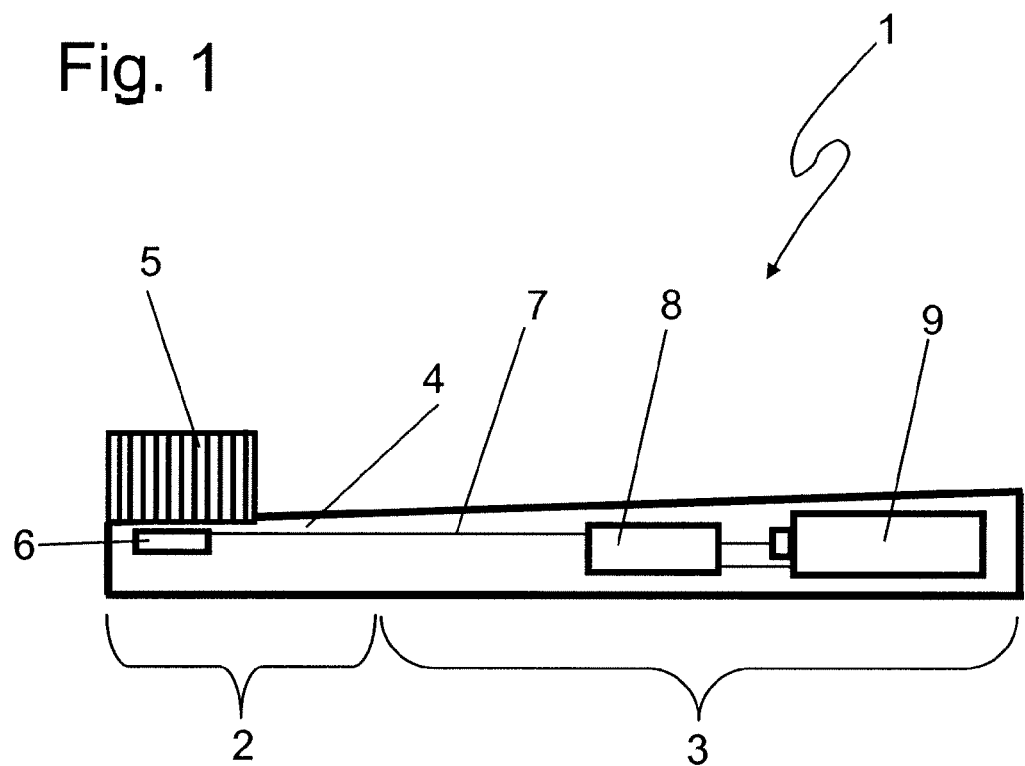
FIG. 1 shows a schematic cross-sectional view of an oral care device in accordance with a first embodiment.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, an oral care device and in particular a head portion of an oral care device may be provided with at least one cleaning element attached to a housing or carrier. In some embodiments, two or more cleaning elements may be provided. In some embodiments, at least one cleaning element may be realized as a bristle tuft comprising at least one filament. In some embodiments at least one cleaning element may be realized as an elastomeric cleaning element.

The cleaning element may be driven into a motion during operation. A motion of the cleaning element may cause tooth paste or liquid, such as water, to be sprayed around when the cleaning element is located outside the mouth of the operator or user.

Generally, oral care devices as disclosed herein may provide the user with information about the time a treatment such as cleaning of the user's oral cavity has already taken and how long it should still take. However, corresponding timers may be started when the oral care device is switched on, disregarding the fact that a switching on of an oral care device does not necessarily imply that the oral care device is already treating the user's oral cavity. Thus the time measured by a timer between switching on and switching off of the oral care device may not correspond to the actual time used for treating the user's oral cavity.

In the accompanying figures identical elements have been denoted by identical reference numbers. While the embodiments depicted in the figures are described with particular configurations shown, the embodiments shown are only given as examples.

While an oral care device may be formed by any device suitable for treating, in particular cleaning a user's teeth, gum or oral cavity it may, for example, be realized as a toothbrush, a tongue cleaner, a flossing device or an oral irrigator. The oral care device may also be any combination of a toothbrush, a tongue cleaner or an oral irrigator.

A head portion in the sense of the present application may be the front part of an oral care device intended for insertion into the user's oral cavity. In some embodiments, the head portion carries at least one cleaning element.

Figure 2:
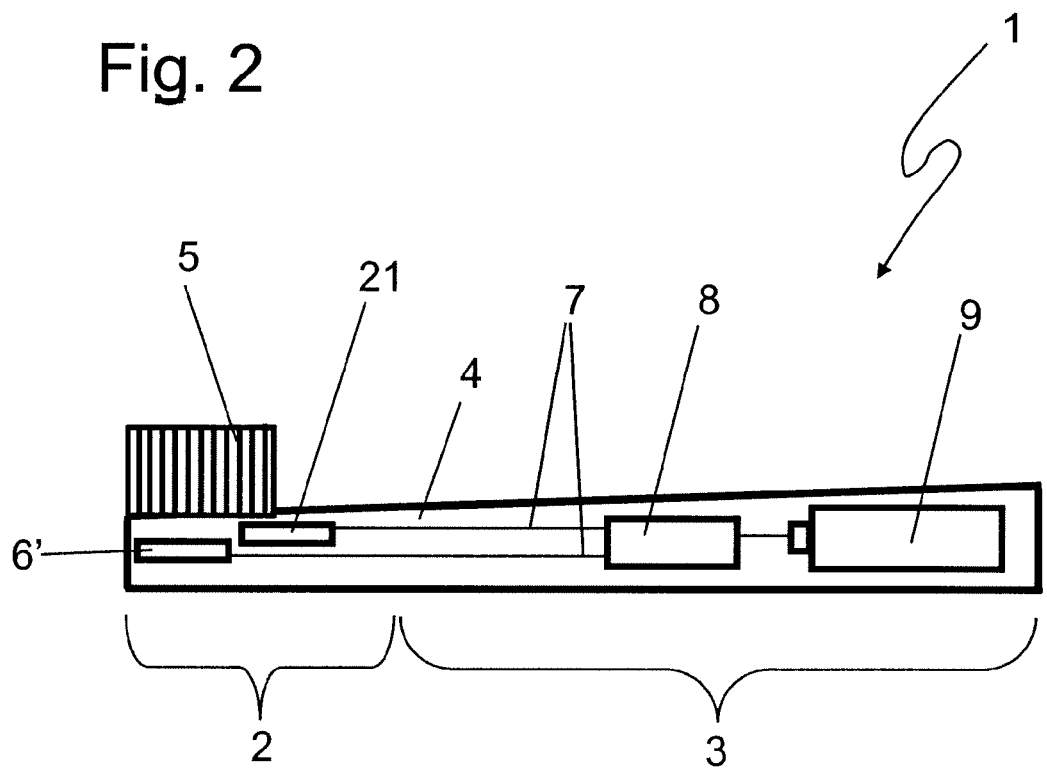
FIG. 2 shows a schematic cross-sectional view of an oral care device in accordance with a second embodiment.

FIGS. 1 and 2 show embodiments in accordance with the present disclosure, wherein the head portion 2 and the handle portion 3 are integrally formed to provide an oral care device realized as a toothbrush 1, and wherein the head portion 2 and the handle portion 3 may not be separated from each other, i.e. they are not removably attached to each other. The head portion 2 may form the front portion of the toothbrush 1.

While in FIGS. 1 and 2 the head portion and the handle portion are integrally formed they may in some embodiments be formed as separate elements being removably attachable to each other. In an alternative embodiment depicted in FIG. 3, the head portion 2 may be a replaceable head portion that is detachably mounted to the handle portion 3.

The housing of the head portion may be a housing having a hollow inner space accommodating mechanical or electrical elements. In some embodiments however, the housing may be a solid part operating as a carrier for the at least one cleaning element without providing any hollow space inside.

In the embodiment of a toothbrush 1 as depicted in FIGS. 1 and 2, the housing 4 of the head portion 2 may be a massive piece of plastic, which may be injection molded together with the handle portion 3.

The exact form and shape of the cleaning element may depend on the type of oral care device considered. A cleaning element arranged thereon may, for example, be a filament, a bristle (of a toothbrush), a jet nozzle (of an oral irrigator) or a scrubbing element (of a tongue cleaner). In some embodiments, the oral care device may be realized as a current emitting device intended for directing a current through the oral cavity during operation. In such an embodiment, the oral care device does not necessarily carry a cleaning element.

While in some embodiments of an oral care device forming a toothbrush, a at least one cleaning element may be a filament formed of an elastic plastic material, for example, a bristle, other forms of cleaning elements for forming a toothbrush may be available. An example for another form of a cleaning element may be a rubber made protrusion extending from the housing of the head portion.

While any suitable material may be utilized in order to form a bristle for a toothbrush, one example for a plastic material suitable for forming a cleaning element or bristle may be polyamide.

In the embodiments depicted in FIGS. 1 and 2, the housing 4 of the head portion 2 acts as a carrier for a plurality of cleaning elements. The cleaning elements in the embodiments depicted may be bristles 5 arranged in tufts. The discussion of embodiments showing cleaning elements arranged at the head portion of the oral care device shall not be limiting for the interpretation of the present disclosure. As was said above, in some embodiment no cleaning element is provided.

A first electrode and a second electrode may form part of a capacitor. The first and/or the second electrode may have different forms and shapes as long as they are made of an electrically conductive material. A simple form may be an extended metallic pad located in or at the head portion. However, the first electrode as well as the second electrode may have other forms and shapes. In some embodiments, the first electrode or the second electrode may be a separate element being dedicated for forming an electrode.

However, there may be some embodiments wherein at least one of the first and second electrodes may be formed by an element simultaneously providing an additional functionality. Such an element in the context of the present disclosure is denoted a functional element. A functional element may form an electrode as long as it comprises an electrically conductive material.

Examples of a functional element also forming an electrode may be a driveshaft of an electric toothbrush located at least partially in the head portion. Another example of a functional element forming an electrode may be a battery for powering the toothbrush located in the handle portion.

In some embodiments, a first electrically conducting path or a second electrically conductive path may be an electrically conductive wire for connecting one of the first or second electrodes to a processor unit. Other examples for electrically conducting paths in the sense of the present disclosure may be an electrically conducting driveshaft or other electrically conducting parts of the head portion or the handle portion.

While in some embodiments an electrode and/or an electrically conducting path may be formed from metal, there may be other examples of electrically conductive material which may be used in order to establish an electrode and/or an electrically conducting path in the sense of the present disclosure. Examples of such other materials may, for example, be electrically conducting plastic materials, electrically conductive coatings applied to plastic material, etc.

In an embodiment, at least one of the first or second electrodes may be formed by a functional element being made of plastic material coated with an electrically conducting coating. In the embodiment depicted in FIG. 1, the first electrode 6 may be formed by a metal plate being connected by a wire 7 to a processor 8. The second electrode according to this embodiment may be formed by the battery 9 powering the processor 8. In some embodiments, the processor unit may be an integrated electronic circuit which may be freely programmable. However, there may be embodiments wherein the processor unit according to the present disclosure is a dedicated electronic circuit provided for performing the necessary functionalities as described below.

A housing of the head portion and/or a housing of the handle portion may at least partly be formed of an electrically isolating material. In some embodiments, at least one of the first electrode and the second electrode is located such that it is isolated by the electrically isolating material of the housing such that it is not exposed to the outside environment of the toothbrush.

This arrangement effectively reduces if not avoids an electrically conducting contact between the electrode and a user's skin or mouth. While the isolation of the electrode by an electrically non-conductive material at least reduces a current flow into the user's body, it nevertheless allows for a measurement of a capacitance formed between the first and second electrodes.

In the embodiments of FIGS. 1 and 2, the first electrode 6 as well as the electrically conducting path formed by the wire 7 are molded directly into the plastic material forming the housing 4 of the head portion 2.

While there may be some embodiments wherein the first and second electrodes forming the capacitor may be both located in the head portion, there may be some other embodiments wherein the first and second electrodes may both be supported in the handle portion. In some other embodiments the first electrode may be located in the head portion and the second electrode may be located in the handle portion.

In the embodiment shown in FIG. 2, the first and second electrodes may both be located in the head portion 2. Both electrodes 6', 21 may be made of metal sheets and may be covered by molded insulating plastic. The two electrodes 6', 21 may be connected to the processor unit 8 by wires 7, which are also molded in the plastic material of the head portion 2 and the handle portion 3.

While there may be embodiments in which the head portion and the handle portion of the toothbrush may be made of a single piece, there may be some embodiments in which the head portion and the handle portion are two separate parts being removably attachable to each other. In such an embodiment, the head portion may be a replaceable portion of an oral care device, wherein its housing may have a mounting section being arranged for removably attaching the housing of the head portion to a handle portion.

Further, the head portion may comprise a first connector being arranged for providing a separable electrical connection to a handle portion. Further, the electrically conducting path may be electrically connecting the first electrode and the first connector. This may allow for detachably mounting the head portion to a handle portion and replacing the head portion once it is worn off.

In some embodiments, the head portion may comprise a second electrode, and a second electrically conductive path for electrically connecting the second electrode to a handle portion. In an embodiment in which the head portion having two electrodes is a replaceable head portion, it may comprise a second connector being arranged for electrically connecting the second conductive path to a handle portion.

In an embodiment of the handle portion according to the present disclosure, the handle portion may further comprise a second electrode being electrically connected to the processor. Thus, the processor may determine a capacitance of a capacitor formed by a first electrode located in the head portion and a second electrode located in the handle portion.

In an embodiment, the handle portion may further comprise a housing, wherein the housing is at least partly formed of an electrically non-conductive material. This may allow for a second electrode being located in the housing such that it is isolated by the electrically isolating material of the housing. This way the second electrode is not exposed to the outside environment of the handle portion.

In some embodiments, the processor unit provided in the handle portion may be arranged such that during operation of the handle portion it compares the capacitance of the capacitor formed by the first electrode and the second electrode with a predetermined threshold value.

According to some embodiments, the value of the capacitance provided by a capacitor formed of the first and second electrodes is used as an indication for whether the head portion is inserted in a user's oral cavity or not. One may assume that inserting the head portion of an oral care device into a user's oral cavity may change the capacitance of the capacitor formed by the first electrode and the second electrode. This may be the case disregarding the question whether the first and second electrodes may be located in the head portion or in the handle portion, but the change in capacitance may be larger and thus better measurable in case at least one of the first and/or second electrodes is arranged in the head portion or extends into a hollow provided in the head portion. In an embodiment, a drive shaft mounted in the handle is used as functional element forming the first electrode and extends into the head portion to drive, for example, a carrier.

In some embodiments, the processor unit may be arranged such that during operation of the handle portion it prevents switching on of a drive in the handle portion once the capacitance determined is above or below a predetermined threshold value. Assuming that the capacitance of the capacitor formed by the first and second electrodes may change once the head portion is located outside the user's mouth compared to a situation where it is in the mouth, switching on of an oral care device having a drive may be inhibited when the head portion is outside of the user's mouth. This at least reduces the risk that an oral care device may be operated outside of the user's oral cavity and thus at least reduces the risk of splattering appliance material such as toothpaste or mouth rinse or fluids in the surrounding of the user. In particular spoiling of clothing and furniture may thus be reduced.

A drive in an oral care device may be an electric motor for providing a motion of part of the head portion, in particular a carrier carrying that may carry at least one cleaning element. However, a drive in the sense of the present disclosure may also be a pump for an oral irrigator.

In some embodiments, the processor unit may be arranged such that during operation of the handle portion it outputs a trigger signal for a timer once the capacitance of the capacitor formed by the first and second electrodes determined is above or below a threshold value.

An oral care device or a handle portion according to some embodiments may provide a timer for indicating to the user that a certain time period for cleaning the teeth has expired and the user may stop the cleaning procedure. In order to do so, the timer may only consider the time during which the head portion of the oral care device is inserted in the user's oral cavity. Thus in one embodiment, the determined capacitance of the capacitor formed by the first and second electrodes may be used as indication for whether the oral care device has been actively operated or not. In some embodiments, the processor unit outputs a trigger signal for a timer once the determined capacitance is above a threshold value, i.e. it is determined that the oral care device has been inserted into the user's mouth. In some embodiments, the processor unit may output a trigger signal for a timer once the capacitance determined is below a threshold value, i.e. it is determined that the oral care device has been withdrawn from the user's mouth.

In some embodiments, the processor unit may be arranged such that during operation of the handle portion it outputs a warning signal once the determined capacitance is above or below a threshold value. A warning signal in the sense of the present disclosure could be any type of signal enabling further processing in another equipment.

In some embodiments, the handle portion may include a mounting section being arranged for removably attaching the handle portion to a head portion and a first connector being arranged for electrically connecting the handle portion to a first electrode located in a head portion. In some embodiments, the combination of a head portion as described before and a handle portion as described before form an oral care device. In some embodiments, the threshold value for the capacitance may be adjusted actively during usage of the toothbrush in order to compensate for any drift.

In some embodiments, in addition to a measurement of the capacitance of the capacitor formed by the first and second electrodes, the drive current may be measured in order to determine different mechanical load on the motor helping to identify situations in which the head portion and in particular the cleaning element is in proximity of the user's oral cavity.

Figure 3:
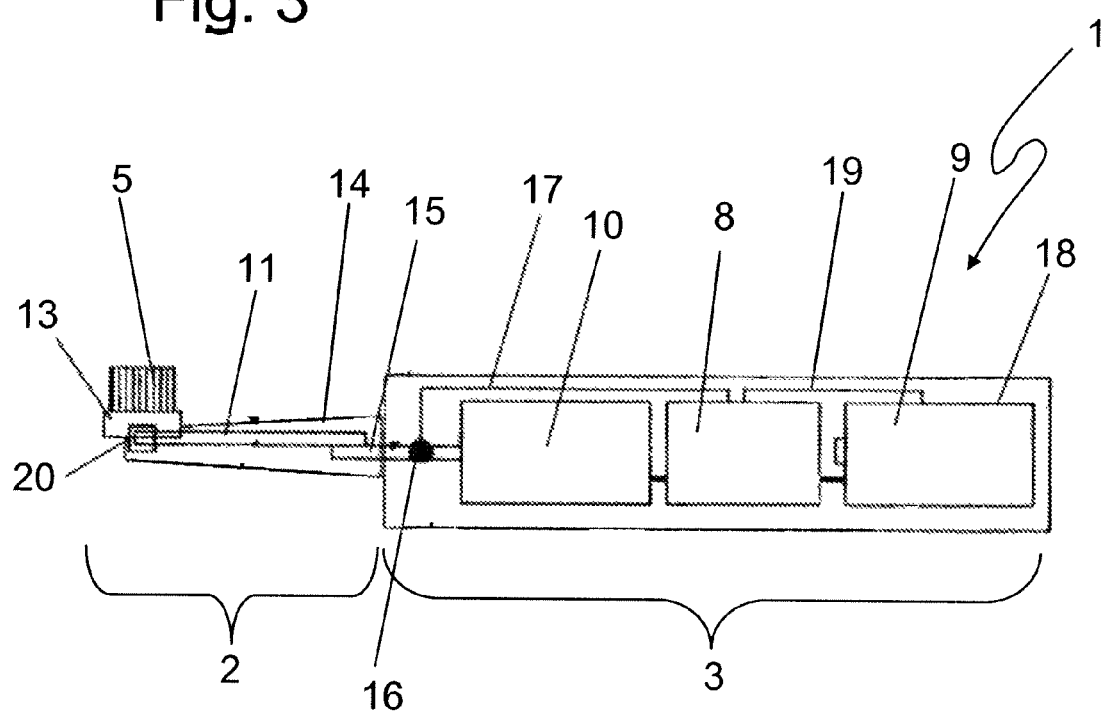
FIG. 3 shows a schematic cross-sectional view of a combination of a detachable head portion and a handle portion according to embodiments shown and described herein.

FIG. 3 shows an electric toothbrush, i.e. an oral care device, in which at least one part of the head portion 2 may be actuated by a motor 10 and via a drive train comprising a drive shaft 15 provided at the handle portion and a drive member 11 provided in the head portion.

In the embodiment of FIG. 3 the part which during operation of the device may be moving is a bristle carrier 13 carrying a plurality of bristles 5. During operation of the toothbrush 1 the bristle carrier 13 and thus the bristles 5 may perform an oscillation pivoting motion around an axis of rotation. The axis of rotation may essentially be perpendicular to the longitudinal extension direction of the head portion 2, i.e. the axis of rotation of the bristle carrier 13 may be essentially parallel to the extension of the bristles 5.

In order to be able to detachably mount the head portion 2 to the handle portion 3 the housing 14 of the head portion 2 may comprise a mounting section being arranged for removably attaching the housing 14 to the handle portion 3. In order to provide for a transfer of the rotating motion of the motor 10 to an oscillating pivoting of the bristle carrier 13 the drive shaft of the motor 10 is attached to a gear and further to a shaft, which may be brought into engagement with the drive member 11 of the head portion 2 when the head portion 2 is attached to the handle portion 3.

Furthermore the head portion 2 may comprise a gear 20 for translating a pivoting oscillation of the drive member 11 around the axis of rotation which is essentially parallel to the longitudinal extension direction of the head portion 2 into an oscillating pivoting around an axis of rotation which is essentially perpendicular to the axis of rotation of the drive member 11.

In the embodiment shown in FIG. 3, the drive member 11 may be made of metal and thus is electrically conducting. The drive member 11 may not only be used in order to transfer the oscillating pivoting of the driveshaft 15 of the handle portion 3 to the bristle carrier 13, but it may also form the first electrode in accordance with an aspect of the present disclosure.

Simultaneously the drive member 11 may form an electrically conductive path connecting the electrode to the driveshaft 15 of the handle portion 3, i.e. in an embodiment the first electrode and the electrically conducting path may be identical. The engagement of the driveshaft 15 of the handle portion 3 and the drive member 11 of the head portion 2 may not only provide for a mechanical coupling, but may also form two electrical connectors being connected to each other once the head portion 2 is attached to the handle portion 3.

In order to connect the drive member 11 and the drive shaft 15 to the processor unit 8 a brush 16 may be in engagement with the driveshaft 15 of the handle portion 3 and connected by a wire 17 to the processor 8. The second electrode in the embodiment as depicted in FIG. 3 may be formed by the battery 9, while in other embodiments it may be formed by any other conductive object inside the handle, for example, by the motor 10. Therefore, in the embodiment shown in FIG. 3, the casing 18 of the battery 9 is connected by a further wire or conductive path 19 to the processor 8. The battery 9 can be used as a power source not only for supplying the required power to the motor 10 but also to the processor unit 8.

The functionality which is described with reference to the flowchart depicted in FIG. 4 in the following is valid for powered and for not powered oral care devices, for example, for powered toothbrushes and for manual toothbrushes.

In step 100 the processor unit 8 may measure the capacitance x of a capacitor formed by a first electrode and a second electrode. This measured capacitance may then be compared in step 101 to a predetermined value z which has been determined in step 102. This predetermined value z for a capacitance may correspond to a threshold value set for distinguishing between a situation in which the head portion is inserted in a user's mouth and a situation in which the head portion is located outside a user's mouth.

Once the head portion is inserted in a user's mouth, wherein at least the first electrode is brought near a dielectric, i.e. the user's teeth and gum, the capacitance may x rise when compared to a situation wherein the head portion is located outside the user's mouth. Accordingly, once the measured capacitance x is larger than the predetermined threshold value z then a warning signal is produced in step 103. This warning signal may start or trigger a timer counting the time during which the toothbrush is used, i.e. the head portion is inserted into the user's mouth.

Once it is determined that the measured capacitance x is smaller than the predetermined threshold value z then in step 104 a trigger signal may be generated for stopping the timer, i.e. to interrupt the counting of the time during which the toothbrush is used. This assumes that when the oral care device, in particular the head portion is not located inside of the user's oral cavity it is not used for cleaning the user's mouth.

Figure 4:
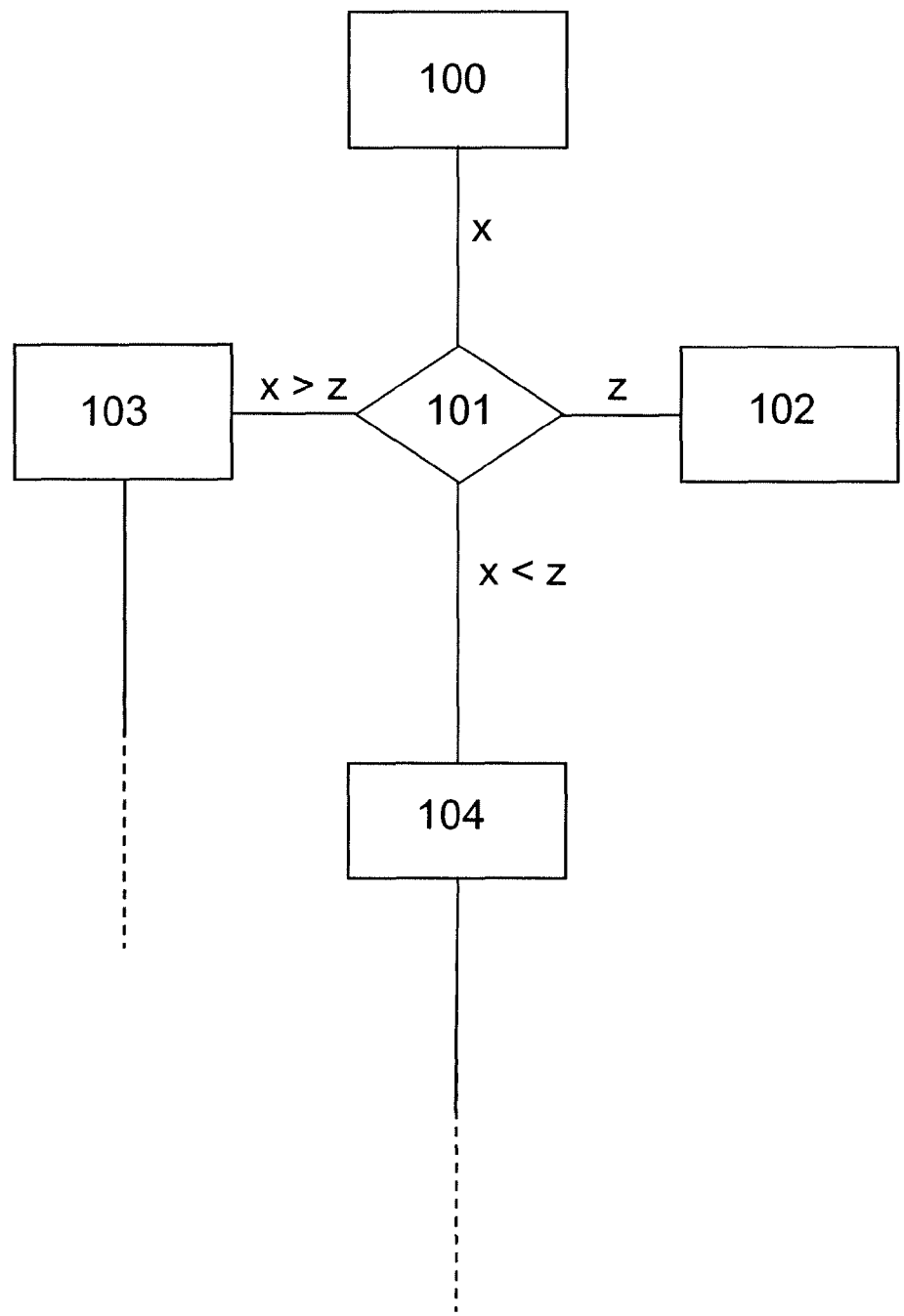
FIG. 4 shows a flowchart of a method in accordance with at least one aspect of the present disclosure.

After steps 103 and 104 the method as depicted in the flowchart of FIG. 4 may be repeated by beginning with step 100 again. In addition to the functionality as described with reference to FIG. 4, a further functionality may be implemented for an embodiment for example as depicted in FIG. 3. In order to avoid that a drive is switched on when the head portion 2 is not inserted into the user's oral cavity in step 104 as depicted in the flow chart of FIG. 4 not only a trigger signal for stopping the timer may be generated, but also the drive may be prevented from being switched on once the measured capacitance x drops below the predetermined threshold value z, i.e. it is determined that the head portion has been removed from the user's oral cavity.

Correspondingly in step 103 the drive may be switched active, i.e. may be switched on to provide an automated operation of the oral care device. While the predetermined threshold value may be a fixed value stored in a memory associated to the processor unit 8 it may also be a value which is initialized by first switching on the toothbrush during a cleaning cycle. As typically a first switching on occurs in the mouth the capacitance measured when the toothbrush is first switched on during a cleaning cycle may be used as the threshold value. In some embodiments, triggering of the initialization of the threshold value may be done by a particular initialization button to be pushed by the user or a certain pattern of one or more buttons to be pushed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A handle portion for an oral-care device comprising the handle portion and a head portion coupled therewith, the handle portion comprising:
   a processor unit connectable to a first electrode and a second electrode of a capacitor;
   a motor; and
   an electrically conducting drive shaft comprising the first electrode and structured to transfer rotating motion of the motor to an oscillating pivoting motion of a bristle carrier;
   wherein the processor unit is arranged such that during operation of the handle portion the processor unit determines a capacitance of a capacitor formed by the first electrode and the second electrode in order to determine whether or not the oral care device is within a user's oral cavity;
   wherein the drive shaft provides both mechanical coupling with the head portion and electrical coupling with the first electrode of the head portion.

2. The handle portion according to claim 1, further comprising:
   a handle housing comprising an electrically isolating material;
   wherein the second electrode is electrically isolated by the electrically isolating material of the handle housing such that it is not exposed to an outside environment of the handle portion.

3. The handle portion according to claim 2, wherein the processor unit is arranged to compare the capacitance to a threshold value during operation of the handle.

4. The handle portion according to claim 3, wherein the processor unit is arranged to prevent switching the drive shaft ON once the capacitance determined is above or below the threshold value.

5. The handle portion according to claim 3, wherein the processor unit is arranged to output a warning signal once the capacitance determined is above or below the threshold value.

6. The handle portion of claim 1 coupled with the head portion, wherein the head portion has a head housing comprising an electrically isolating material; a moveable drive member defining at least a portion of the first electrode; and a first electrically conducting path for connecting the first electrode to the processor unit;
   wherein the first electrode is electrically isolated by the electrically isolating material of the head housing such that it is not exposed to an outside environment of the head portion; the drive member including mechanical and electrical coupling for attachment to the handle portion of the oral care device.

7. An oral-care device comprising:
   a housing being at least partially formed of an electrically isolating material
   a processor unit;
   a capacitor having a first electrode and a second electrode, the first and second electrodes being electrically isolated by the electrically isolating material of the housing such that they are not exposed to an outside environment of the oral care device; and
   a head portion including a head housing comprising an electrically isolating material, a moveable drive member, the first electrode for forming part of a capacitor, and a first electrically conducting path for connecting the first and second electrodes to the processor unit;
   wherein the processor unit is arranged to determine a capacitance of the capacitor during operation in order to determine whether or not the oral care device is within a user's oral cavity;
   wherein the oral-care device includes an electrically conducting drive shaft that forms the first electrode,
   wherein the first electrode is electrically isolated by the electrically isolating material of the head housing such that it is not exposed to an outside environment of the head portion; and
   wherein the drive member forms at least part of the first electrode, the drive member including a mechanical and electrical coupling for attachment to a handle portion of the oral care device.

8. An oral-care device having a bristle carrier and comprising a handle portion and a head portion attachable to the handle portion,
   wherein the handle portion includes a processor unit connectable to a first electrode and a second electrode forming a capacitor, the processor unit being arranged to determine, during operation, a capacitance of the capacitor in order to determine whether the oral-care device is within a user's oral cavity,
   a motor and a drive shaft for transferring a rotating motion of the motor to an oscillating pivoting motion of the bristle carrier, wherein the drive shaft comprises the first electrode, the drive shaft providing both mechanical coupling and electrical coupling between the handle portion and the head portion;

wherein the head portion includes a head housing comprising an electrically isolating material, a moveable drive member comprising the first electrode, and a first electrically conducting path for connecting the first electrode to the processor unit;

wherein the first electrode is electrically isolated by the electrically isolating material of the head housing such that the first electrode is not exposed to an outside environment of the head portion, and wherein the movable drive member includes a mechanical coupling and electrical coupling for attachment to the handle portion.

\* \* \* \* \*